(12) United States Patent
Liu et al.

(10) Patent No.: US 8,583,259 B2
(45) Date of Patent: Nov. 12, 2013

(54) ELECTRODE LEAD AND PACEMAKER USING THE SAME

(75) Inventors: Liang Liu, Beijing (CN); Li Fan, Beijing (CN); Wen-Mei Zhao, Beijing (CN); Chen Feng, Beijing (CN); Yu-Quan Wang, Beijing (CN); Li Qian, Beijing (CN)

(73) Assignees: Tsinghua University, Beijing (CN); Hon Hai Precision Industry Co., Ltd., New Taipei (TW)

( * ) Notice: Subject to any disclaimer, the term of this patent is extended or adjusted under 35 U.S.C. 154(b) by 0 days.

(21) Appl. No.: 13/527,849

(22) Filed: Jun. 20, 2012

(65) Prior Publication Data

US 2013/0110217 A1 May 2, 2013

(30) Foreign Application Priority Data

Oct. 28, 2011 (CN) .......................... 2011 1 0333560

(51) Int. Cl.
*A61B 1/04* (2006.01)

(52) U.S. Cl.
USPC ........................................ 607/119

(58) Field of Classification Search
USPC .................................................. 607/118, 119
See application file for complete search history.

(56) References Cited

U.S. PATENT DOCUMENTS 7,383,091 B1 * 6/2008 Chitre et al. ................... 607/127
7,493,160 B2 * 2/2009 Weber et al. ...................... 607/3

* cited by examiner

*Primary Examiner* — George Manuel
(74) *Attorney, Agent, or Firm* — Altis & Wispro Law Group, Inc.

(57) ABSTRACT

An electrode lead of a pacemaker includes a metal conductive core, a carbon nanotube film, and an insulator. The metal conductive core defines an extending direction. The carbon nanotube film at least partially surrounds the metal conductive core and is electrically insulated from the metal conductive core. The insulator is located between the metal conductive core and the carbon nanotube film. The carbon nanotube film includes a plurality of carbon nanotubes substantially extending along the extending direction of the metal conductive core. A bared part is defined at one end of the electrode lead. A pacemaker using the above mentioned electrode lead is also disclosed.

20 Claims, 6 Drawing Sheets

ELECTRODE LEAD AND PACEMAKER USING THE SAME

RELATED APPLICATIONS

This application claims all benefits accruing under 35 U.S.C. §119 from China Patent Application No. 201110333521.5, filed on Oct. 28, 2011 in the China Intellectual Property Office, the disclosure of which is incorporated herein by reference.

BACKGROUND

1. Technical Field

The present disclosure relates to an electrode lead based on carbon nanotubes and a pacemaker using the electrode lead.

2. Discussion of Related Art

Pacemakers are electronic therapeutic devices which can be implanted into human bodies. The pacemakers can emit pulse currents to stimulate organs.

The pacemaker includes a pulse generator and an electrode lead. The pulse generator is electrically connected with the electrode lead. The electrode lead includes a connector, an electrode lead, and an electrode tip. The connector is electrically connected with the pulse generator. The connector and the electrode tip are located at two opposite ends of the electrode lead. The electrode lead includes a plurality of metal wires. The connector and the electrode tip are electrically connected with the metal wires. However, the electrode lead composed of the metal wires has poor strength and ductility, and is easily broken due to repeat distortions. Thus, the lifetimes of the lead electrode and the pacemaker using the lead electrode are reduced.

What is needed, therefore, is to provide an electrode lead and a pacemaker using the same, which can overcome the shortcomings as discussed above.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
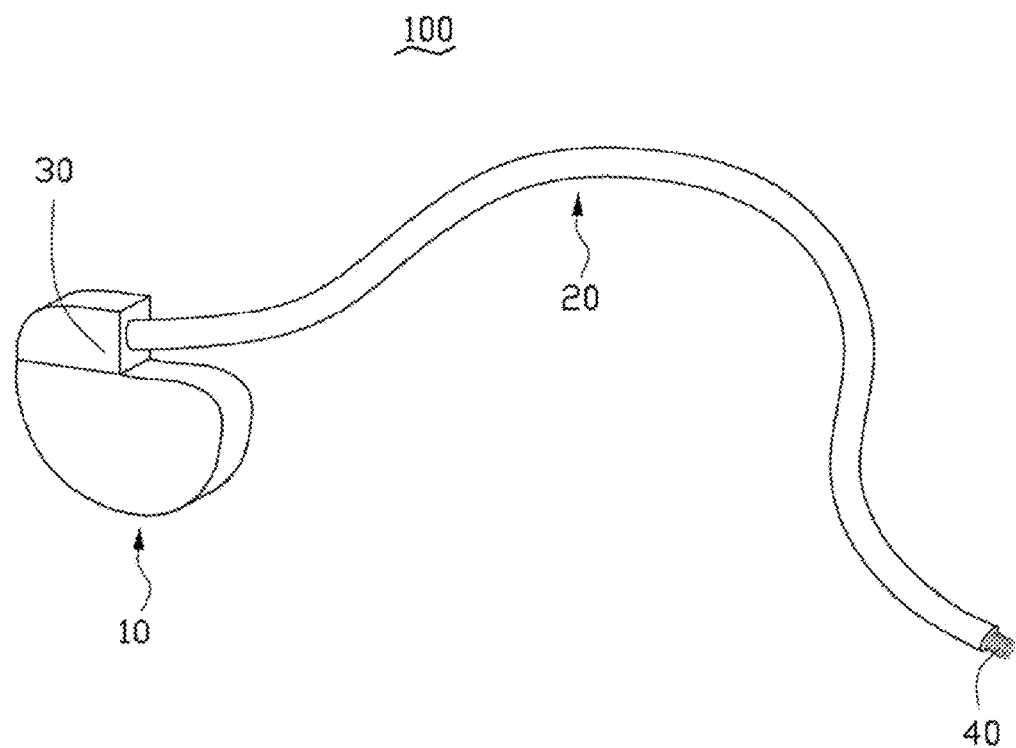
FIG. 1 is a schematic view of one embodiment of a heart pacemaker.

Referring to FIG. 1, one embodiment of a pacemaker 100 includes a pulse generator 10 and an electrode lead 20 electrically connected with the pulse generator 10. The electrode lead 20 has a connector 30 and a bared part 40 opposite to the connector 30. The electrode lead 20 has a proximal end and a distal end opposite to the proximal end. The connector 30 is located at the proximal end the electrode lead 20, and the bared part 40 is located at the distal end of the electrode lead 20. The electrode lead 20 is electrically connected with the pulse generator 10 through the connector 30. The pulse generator 10 can generate pulse signals to stimulate organs of living beings via the electrode lead 20.

The pulse generator 10 can include a shell (not labeled), a power source (not shown), and a control circuit (not shown). The power source and the control circuit are packaged in the shell. The power source can provide power for the control circuit. Batteries can be used as the power source, such as lithium ion batteries, fuel cells, and physical power batteries. In one embodiment, a lithium-iodine battery is the power source. The control circuit can include an output circuit and a sensing circuit. The output circuit can be used to generate the pulse signals. The sensing circuit can be used to receive electrical signals generated by the stimulated organs and feed these electrical signals back to the output circuit. The output circuit can adaptively adjust to output proper pulse signals according to the feedback of the sensing circuit. The organs can be a heart, brain, or stomach of living beings. In one embodiment, the organ is the heart of a human being. The pulse signals can be a square wave pulsing current. A pulse width of the pulse signals can be in a range from about 0.5 milliseconds to about 0.6 milliseconds. The pulse current can be generated by a charging-discharging process of a capacitor in the control circuit. The shell used for packaging can prevent an interaction between the power source, the control circuit and the living being in which the pacemaker is implanted. A material of the shell can be a metal or alloy, which is biocompatible, corrosion resistant, and structurally tough or rigid. In one embodiment, the material of the shell is titanium.

Figure 2:
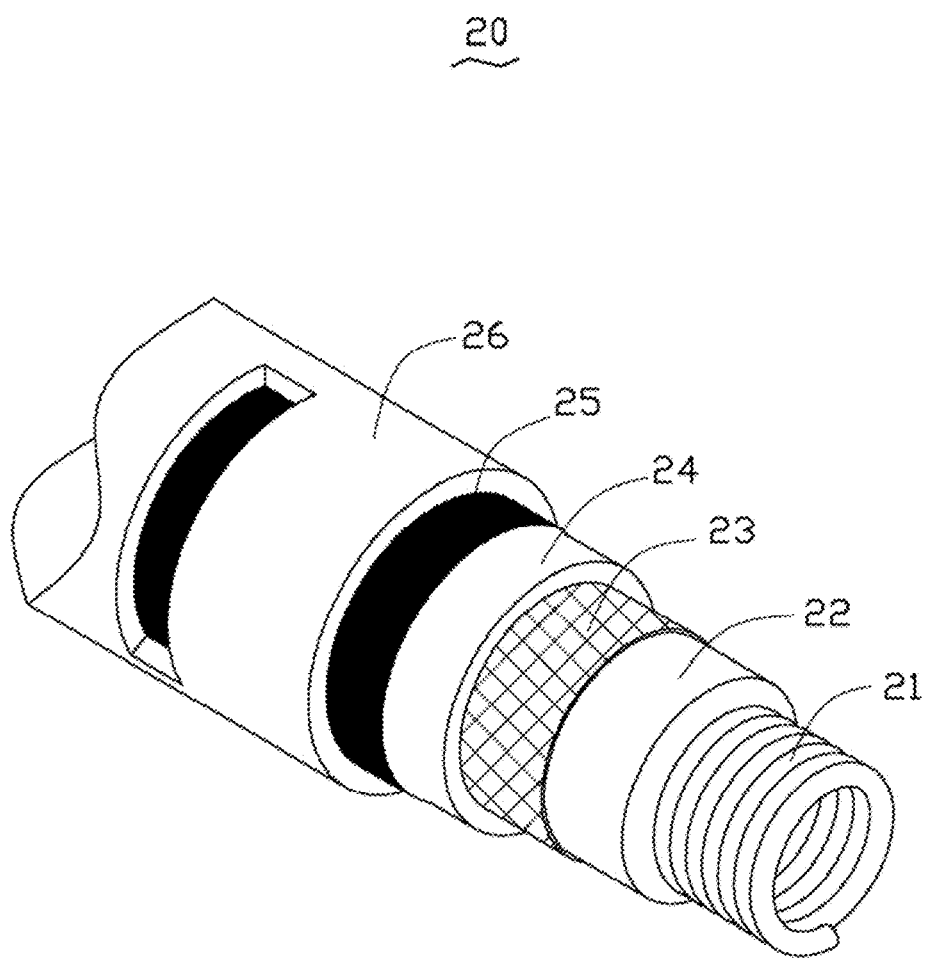
FIG. 2 is a stepped, cross-sectional view of part of the electrode lead shown in FIG. 1.

The electrode 20 can include a metal conductive core, a carbon nanotube film, and an insulator (not labeled) located between the metal conductive core and the carbon nanotube film. The insulator can include a first insulated layer, a shield layer, and a second insulated layer. Referring FIG. 2, the electrode lead 20 can include a metal conductive core 21, a first insulated layer 22 winding round the metal conductive core 21, a shield layer 23 wrapping around the first insulated layer 22, a second insulated layer 24 winding around the shield layer 23, a carbon nanotube film 25 wrapping round the second insulated layer 24, and a coating layer 26 winding around the carbon nanotube film 25. A part of the carbon nanotube film 25 is exposed through the coating layer 26. The carbon nanotube film 23 includes a number of carbon nanotubes substantially oriented along a same direction. The carbon nanotubes substantially extend along an axial direction of the metal conductive core 21.

The electrode lead 20 can further include a ring electrode (not shown) located on the carbon nanotube film 25 exposed from the coating layer 26. The ring electrode is electrically connected with the carbon nanotube film 25.

The bared part 40 is a part of the metal conductive core 21 exposed from the first insulated layer 22, the shield layer 23, the second insulated layer 24, the carbon nanotube film 25, and the coating layer 26 in order. A length of the bared part 40 can range from about 0.5 millimeters to about 2 millimeters.

The shape of the bared part 40 is spiral. The bared part 40 acts as an electrode head of the electrode lead 20. In use, the bared part 40 contacts living cells and carries pulse current signals generated from the pulse generator 10 to the cells. The bared part 40 acts as both the stimulating electrode and the sensing electrode. The bared part 40 can be fixed to an organ and tissue to prevent the electrode lead 20 from sliding or falling off the organ and tissue.

The metal conductive core 21 can be a hollow spiral structure with a certain elasticity to improve the lifetime of the electrode lead 20. The hollow spiral structure is formed by twisting the linear shaped metal conductive core 21. In one embodiment, the metal conductive core 21 is spirally twisted around a linear supporter, and then the linear supporter is removed to form the hollow spiral metal conductive core 21. A diameter of a coil formed by the hollow spiral metal conductive core 21 can range from about 4 millimeters to about 6 millimeters. In one embodiment, the diameter of the coil is about 5 millimeters. A thread pitch of the hollow spiral conductive structure 21 can be in a range from about 0 millimeters to about 10 millimeters. In one embodiment, the thread pitch is about 0 millimeters. In other embodiments, the metal conductive core 21 is a linear structure with a solid structure or a hollow structure.

The metal conductive core 21 has good electrical conductivity. A material of the metal conductive core 21 can be MP35N®, 35NLT®, stainless steel, carbon fiber, tantalum, titanium, zirconium, niobium, titanium alloy, copper, silver, platinum, platinum-yttrium alloy, or platinum-palladium alloy. MP35N® is an alloy including 35Co-35Ni-20Cr-10Mo, with a weight percentage of titanium being about 1% in the MP35N®. 35NLT® is also an alloy including 35Co-35Ni-20Cr-10Mo with a weigh percentage of titanium being about 0.01% in the 35NLT®. In one embodiment, the material of the metal conductive core 21 can be platinum.

Materials of the first and second insulated layers 22, 24 can be silicone, polyurethane, polytetrafluoroethylene, silicone-polyurethane copolymer, polyethylene, polypropylene, polystyrene, polystyrene foam, or nanoclay-polymer composite material. The polymer material in the nanoclay-polymer composite material can be silicone, polyurethane, or polyolefin such as polyethylene or polypropylene. In one embodiment, the first and second insulated layers 22, 24 are made of polystyrene foam. The materials of the first insulated layer 22 and the second insulated layer 24 are not limited, as long as the first and second insulated layers 22, 24 can function as electrical insulators.

The shield layer 23 shields electromagnetic interference or outer signal interference. A material of the shield layer 23 can be an electrical conductive material, such as metal or carbon nanotubes. In one embodiment, the shield layer 23 consists of copper.

Figure 3:
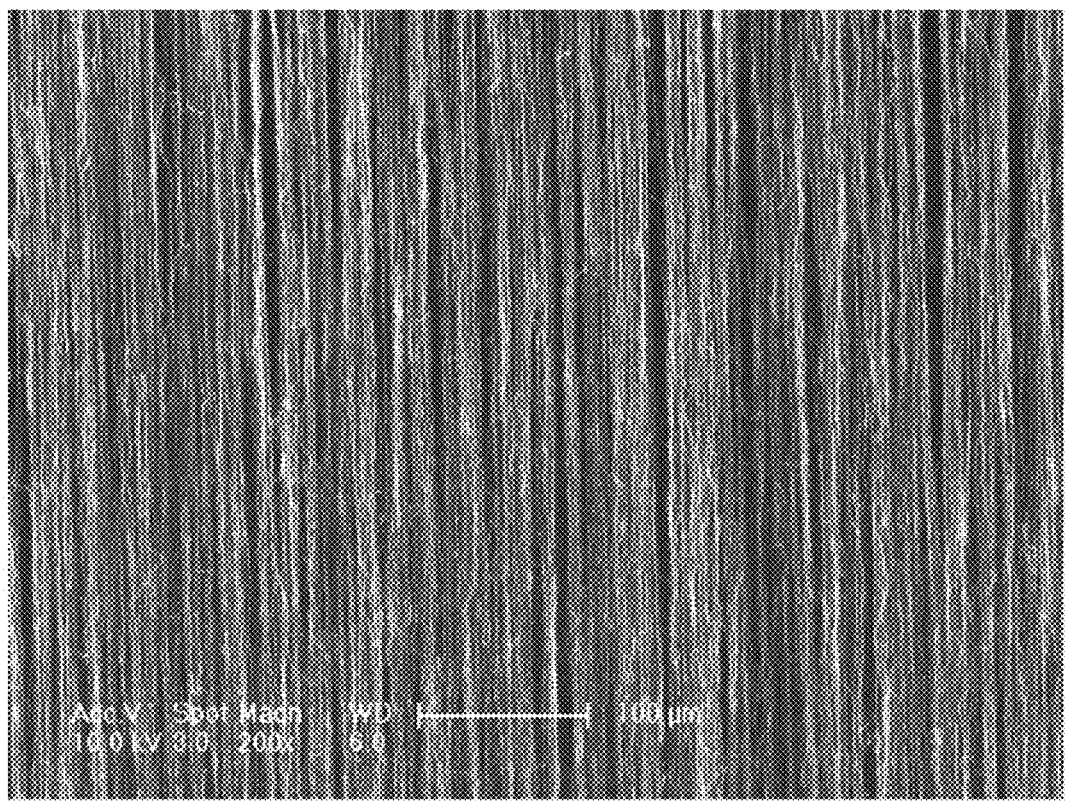
FIG. 3 shows a scanning electronic microscope (SEM) image of a carbon nanotube film used in FIG. 1.

Referring to FIG. 3, the carbon nanotube film 25 is a free-standing film. The carbon nanotube film 25 includes a plurality of carbon nanotubes that can be arranged substantially parallel to a surface of the carbon nanotube film. A large number of the carbon nanotubes in the carbon nanotube film can be oriented along a preferred orientation, meaning that a large number of the carbon nanotubes in the carbon nanotube film are arranged substantially along a same direction. In the carbon nanotube film, an end of one carbon nanotube is joined to another end of an adjacent carbon nanotube arranged substantially along the same direction by van der Waals attractive force. A small number of the carbon nanotubes are randomly arranged in the carbon nanotube film, and has a small if not negligible effect on the larger number of the carbon nanotubes in the carbon nanotube film arranged substantially along the same direction. The carbon nanotubes oriented substantially along the same direction may not be perfectly aligned in a straight line, and some curve portions may exist. It can be understood that some carbon nanotubes located substantially side by side in contact with each other cannot be excluded.

Figure 4:
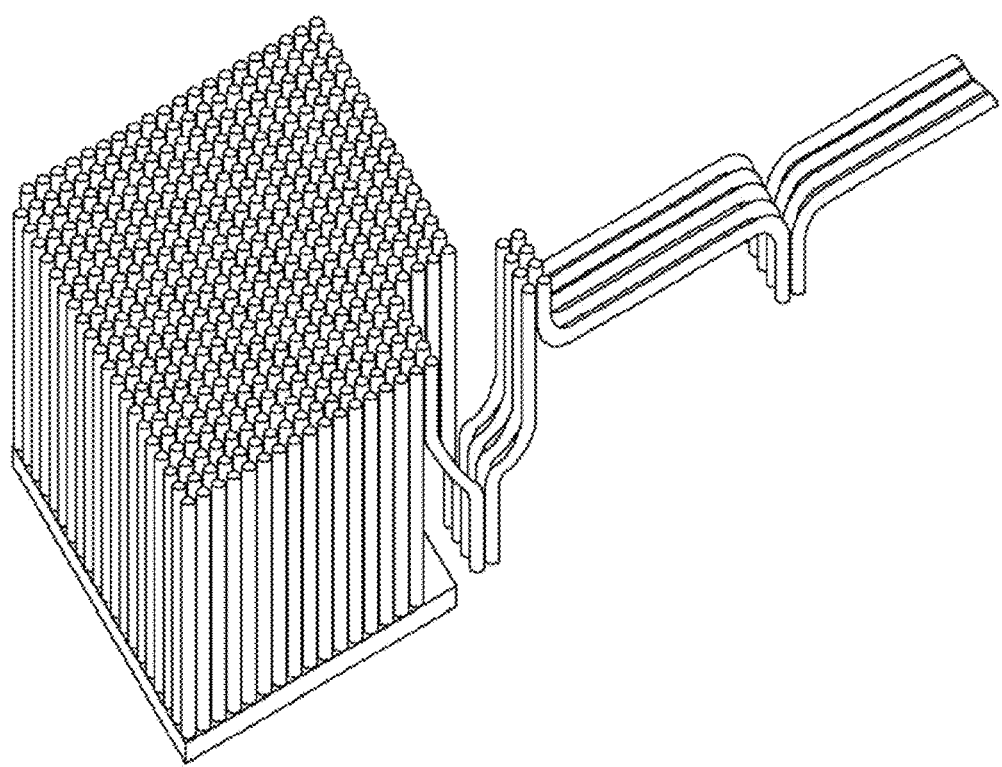
FIG. 4 shows a process schematic view for making the carbon nanotube film shown in FIG. 4 from a carbon nanotube array.

Referring to FIG. 4, a method for making the carbon nanotube film 25 can include:

S1, providing a carbon nanotube array; and

S2, selecting a carbon nanotube segment from the carbon nanotube array using a tool, and drawing the carbon nanotube segment at a predetermined speed, thereby pulling out a continuous carbon nanotube drawn film including a plurality of carbon nanotube segments joined end-to-end by van der Waals attractive force therebetween.

In step S1, the carbon nanotube array is formed on a substrate. The carbon nanotube array consists of carbon nanotubes. The carbon nanotubes can be single-wall carbon nanotubes, double-wall carbon nanotubes, multi-wall carbon nanotubes, or any combinations thereof. Diameters of the carbon nanotubes can be from about 0.5 nanometers to about 50 nanometers. Lengths of the carbon nanotubes can be from about 50 nanometers to about 5 millimeters. In one embodiment, the lengths of the carbon nanotubes can be from about 100 micrometers to about 900 micrometers. In one embodiment, the carbon nanotubes are multi-wall carbon nanotubes, and the carbon nanotubes are substantially parallel to each other and substantially perpendicular to the substrate. The carbon nanotube array is essentially free of impurities, such as carbonaceous or residual catalyst particles. The carbon nanotube array can be a super aligned carbon nanotube array. A method for making the carbon nanotube array is unrestricted, and can be by chemical vapor deposition methods or other methods.

In step S2, the pulling direction can be substantially perpendicular to the growing direction of the carbon nanotube array. During the pulling process, as the initial carbon nanotube segments are drawn out, other carbon nanotube segments are also drawn out end to end due to van der Waals force between ends of adjacent segments. This process of pulling produces a substantially continuous and uniform carbon nanotube film having a predetermined width.

A method for wrapping the carbon nanotube film 25 around the second insulated layer 24 includes drawing a carbon nanotube film from a carbon nanotube array. One end of the carbon nanotube film is adhered to an outer surface of the second insulated layer 24, and the carbon nanotubes in the carbon nanotube film substantially extend along the axial direction of the metal conductive core 21. The carbon nanotube film or the metal conductive core 21 with the second insulated layer 24 is rotated to wind the carbon nanotube film around the outer surface of the second insulated layer 24. The carbon nanotube film has a large surface, therefore the carbon nanotube film can adhere to the second insulated layer 24 by van der Waals force. In one embodiment, an adhesive layer is coated on the second insulated layer 24, and then the carbon nanotube film is adhered to the second insulated layer 24 by the adhesive layer.

The coating layer 26 can be fabricated by a biocompatible material, such as silicone or polyurethane. In one embodiment, the material of the coating layer 26 is polyurethane.

A working process of the pacemaker 100 acting on a heart described below. The electrode lead 20 is implanted to the heart of a human with the bared part 40 used as the electrode head contacting the heart. The pulse signals are generated by the pulse generator 10 and transmitted to the bared part 40 to stimulate the heart. A heartbeat frequency or a series of heartbeat frequencies can be sensed by detecting potential differences between the bared part 40 and the pulse generator 10. The potential differences are fed back to the pulse generator 10 to adjust the pulse signals to make the heart beat normally.

The carbon nanotubes have excellent mechanical strength and toughness. Accordingly, the carbon nanotube film 25 consisting of the carbon nanotubes have excellent mechanical strength and toughness. If the electrode lead 20 is stretched by a drawing force, the metal conductive core 21 will be elongated along the stretching direction. The carbon nanotube film 25 wrapping around the metal conductive core 21 can prevent the metal conductive core 21 from breaking due to a friction force between the carbon nanotube film 25 and the metal conductive core 21. Thus, the electrode lead 20 does not break easily under the same drawing force, and the electrode lead 20 is still electrically conductive. The mechanical strength, toughness, and life of the electrode lead 20 are improved.

The carbon nanotubes in the carbon nanotube film 23 extend substantially along the extending direction of the metal conductive core 21. The carbon nanotubes have good electrical conductivity along the extending direction of the carbon nanotubes because the carbon nanotube axial conductivity is excellent and the carbon nanotube axial conductive path is short. Therefore, the electrical conductivity of the electrode lead 20 can be improved. Thus, the sensitivity and the efficiency of the pacemaker 100 are improved.

Figure 5:
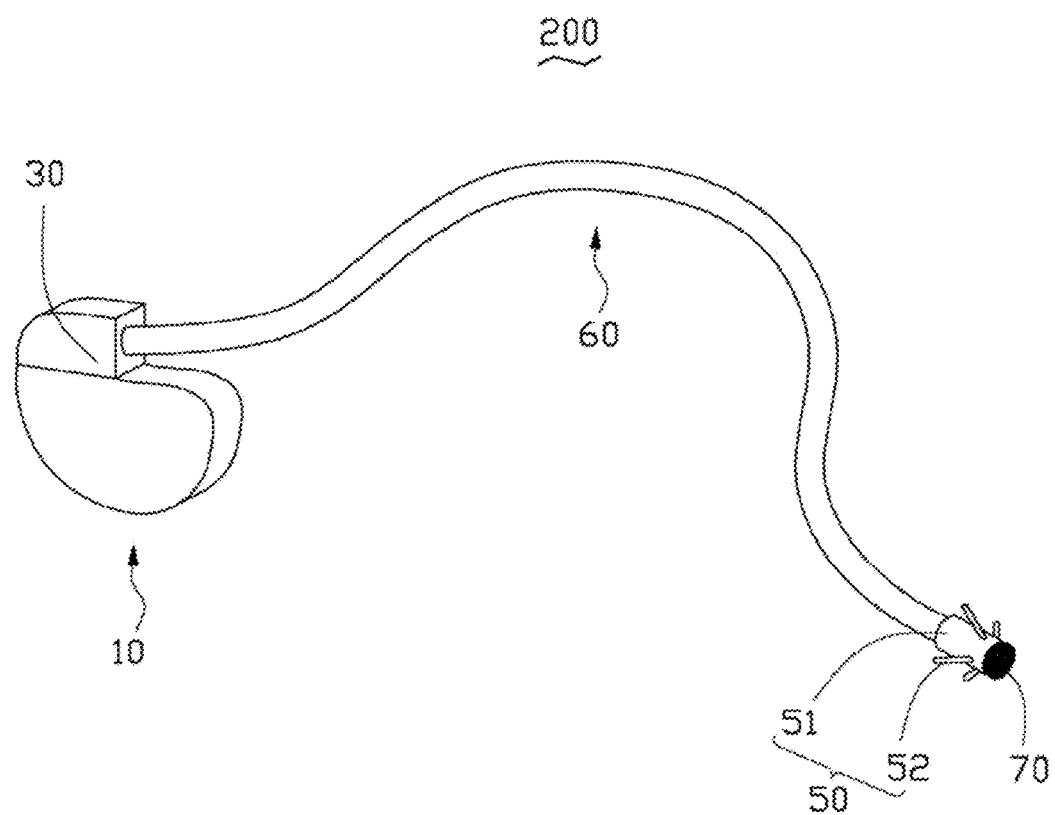
FIG. 5 shows a schematic view of one embodiment of a heart pacemaker.
Figure 6:
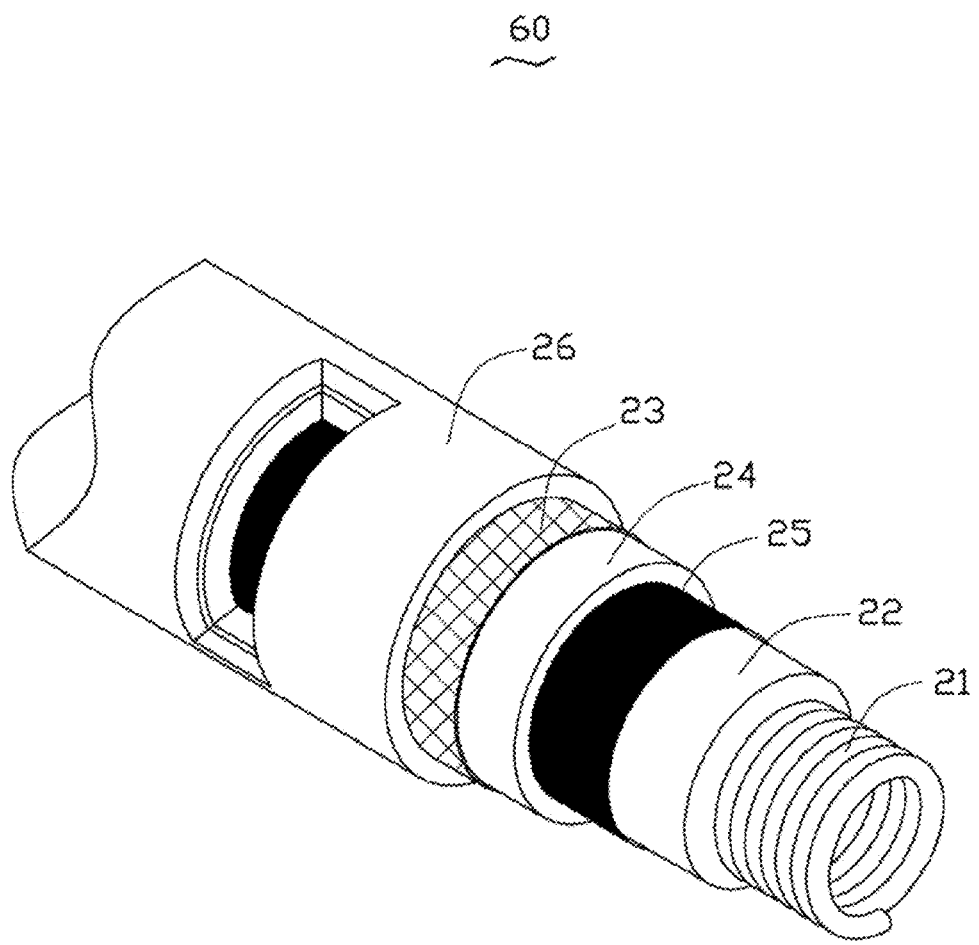
FIG. 6 is a stepped, cross-sectional view of part of the electrode lead shown in FIG. 5.

Referring to FIG. 5 and FIG. 6, one embodiment of a pacemaker 200 is also provided. The pacemaker 200 includes a pulse generator 10 and an electrode lead 60. The electrode lead 60 includes a proximal end and a distal end opposite to the proximal end. A connector 30 is at the proximal end the electrode lead 60, and the bared part (not labeled) is the distal end of the electrode lead 60.

The electrode lead 60 includes the metal conductive core 21, the first insulated layer 22 winding around the metal conductive core 21, the carbon nanotube film 25 wrapping around the first insulated layer 22, the second insulated layer 24 winding around the carbon nanotube film 25, the shield layer 23 wrapping around the second insulated layer 24, and the coating layer 26 winding around the shield layer 23; and the electrode lead 60. A part of the carbon nanotube film 25 is exposed from the second insulated layer 24, the shield layer 23 and the coating layer 26 in order.

The electrode lead 60 can include a ring electrode (not shown) located on the exposed part of the carbon nanotube film 25. The ring electrode is exposed from the second insulated layer 24, the shield layer 23, and the coating layer 26. The ring electrode is electrically connected with the carbon nanotube film 25.

The electrode lead 60 can further include an electrode head 70 fixed on the bared part. The electrode head 70 is electrically connected with the electrode lead 60. Thus, the electrode head 23 can be used to transfer the pulse signals produced from the pulse generator 10 to the organ of the human body, to stimulate the organ of the human body.

A material of the electrode head 70 can be metal or alloy having an excellent conductivity, such as platinum-iridium alloy. A porous material to ensure biocompatibility can be coated on an outer surface of the electrode head 70. In addition, the porous material can increase the contact area between the electrode head 70 and the human body, thereby increasing the sensitivity and sensing efficiency of the pacemaker. The porous material can be activated carbon, carbon fiber, carbon nanotubes, or titanium-nitrogen alloy.

The electrode lead 60 can further include a fixture 50 located on the distal end of the electrode lead 60. Thus, the fixture 50 can be opposite to and away from the connector 30. A material of the fixture 50 can be a polymer, such as polyurethane or silicon rubber. The fixture 50 can include a fixing ring 51 and a plurality of fixing wings 52. The fixing ring 51 can be a cylindrical structure. The plurality of fixing wings 52 can be rod-shaped. The plurality of fixing wings 52 forms a branch axis diverging from a center line or axis of the fixing ring 51, to form a barb structure. A diverging direction deviates from the extending direction of the electrode lead 20. An angle between the extending direction of each fixing wing 52 and the center line of the fixing ring 51 can be in a range from about 30 degrees to about 60 degrees. The fixture 50 can be fixed to the organ with the fixing wings 52 wrapped around by the fibrous tissue. The fixture 50 can also be a protrusion or helical structure as long as the electrode lead 20 can be tightly fixed to the organ by fibrous tissues.

Other characteristics of the pacemaker 200 are the same as those of the pacemaker 100.

It is to be understood that the above-described embodiment is intended to illustrate rather than limit the disclosure. Variations may be made to the embodiment without departing from the spirit of the disclosure as claimed. The above-described embodiments are intended to illustrate the scope of the disclosure and not restricted to the scope of the disclosure.

It is also to be understood that the above description and the claims drawn to a method may include some indication in reference to certain steps. However, the indication used is only to be viewed for identification purposes and not as a suggestion as to an order for the steps.

What is claimed is:

1. An electrode lead of a pacemaker, comprising:
    a metal conductive core defining an extending direction;
    a carbon nanotube film at least partially surrounding the metal conductive core and electrically insulated from the metal conductive core; and
    an insulator located between the metal conductive core and the carbon nanotube film, the insulator electrically insulating the carbon nanotube film from the metal conductive core,
    wherein the carbon nanotube film comprises a plurality of carbon nanotubes substantially extending along the extending direction of the metal conductive core; an end of the metal conductive core defines a bared part configured to be electrically connected to an organ.

2. The electrode lead of claim 1, wherein the metal conductive core is a hollow spiral structure.

3. The electrode lead of claim 1, wherein the bared part is exposed from the insulator and the carbon nanotube film.

4. The electrode lead of claim 1, further comprising an electrode head electrically connected with the bared part.

5. The electrode lead of claim 4, further comprising a fixture located on the electrode lead close to the electrode head, wherein the fixture is configured to fix the electrode lead to the organ.

6. The electrode lead of claim 5, wherein the fixture comprises a fixing ring and a plurality of fixing wings, the plurality of fixing wings forms a branch axis diverging from a center line of the fixing ring, and an angle between an extending direction of each of the plurality of fixing wings and the center line of the fixing ring is in a range from about 30 degrees to about 60 degrees.

7. The electrode lead of claim 1, wherein a part of the carbon nanotube film is exposed from the electrode lead.

8. The electrode lead of claim 7, further comprising a sensing electrode located on the part of the carbon nanotube film exposed from the electrode lead.

9. The electrode lead of claim 1, wherein the insulator comprises:
a first insulated layer surrounding the metal conductive core;
a shield layer wrapping around the first insulated layer;
a second insulated layer winding around the shield layer, wherein the carbon nanotube film is wrapped around the second insulated layer; and
a coating layer winding around the carbon nanotube film, wherein a part of the carbon nanotube film is exposed from the coating layer.

10. The electrode lead of claim 9, wherein the carbon nanotube film is adhered to the second insulated layer by van der Waals force.

11. The electrode lead of claim 9, wherein the carbon nanotube film is adhered to the second insulated layer by an adhesive layer.

12. The electrode lead of claim 1, wherein the insulator comprises:
a first insulated layer surrounding the metal conductive core, wherein the carbon nanotube film is wrapped around the first insulated layer;
a second insulated layer winding around the carbon nanotube film;
a shield layer wrapping around the second insulated layer; and
a coating layer winding around the shield layer,
wherein a part of the carbon nanotube film is exposed through the second insulated layer, the shield layer, and the coating layer.

13. The electrode lead of claim 12, wherein the carbon nanotube film is adhered to the second insulated layer by van der Waals force or an adhesive layer.

14. The electrode lead of claim 12, wherein the bared part is exposed from the first insulated layer, the carbon nanotube film, the second insulated layer, the shield layer, and the coating layer.

15. The electrode lead of claim 1, wherein the plurality of carbon nanotubes are joined end-to-end by van der Waals force along axes of the plurality of carbon nanotubes.

16. A pacemaker, comprising a pulse generator producing a pulse signal and
an electrode lead transmitting the pulse signal, the electrode lead comprising:
a metal conductive core defining an extending direction;
a carbon nanotube film at least partially surrounding the metal conductive core; and
an insulator located between the metal conductive core and the carbon nanotube film, the insulator electrically insulating the carbon nanotube film from the metal conductive core,
wherein the carbon nanotube film comprises a plurality of carbon nanotubes substantially extending along the extending direction of the metal conductive core; an end of the metal conductive core defines a bared part configured to be electrically connected to an organ.

17. The pacemaker of claim 16, wherein a part of the carbon nanotube film is exposed through the electrode lead.

18. The pacemaker of claim 17, wherein the electrode lead further comprises a sensing electrode located on the part of the carbon nanotube film which is exposed through the electrode lead.

19. The pacemaker of claim 16, wherein the electrode lead further comprises a fixture located on the bared part, and the fixture is configured to fix the electrode lead to the organ.

20. The pacemaker of claim 16, wherein the plurality of carbon nanotubes are joined end-to-end by van der Waals force along the extending direction of the metal conductive core

* * * * *